(12) United States Patent
Petito

(10) Patent No.: US 6,541,460 B2
(45) Date of Patent: Apr. 1, 2003

(54) METHOD FOR USE OF HYALURONIC ACID IN WOUND MANAGEMENT

(76) Inventor: George D. Petito, 1890 Bucknell Dr., Bethlehem, PA (US) 18015

( * ) Notice: Subject to any disclaimer, the term of this patent is extended or adjusted under 35 U.S.C. 154(b) by 0 days.

(21) Appl. No.: 10/252,396

(22) Filed: Sep. 24, 2002

(65) Prior Publication Data

US 2003/0021834 A1 Jan. 30, 2003

Related U.S. Application Data

(63) Continuation-in-part of application No. 09/219,456, filed on Dec. 23, 1998, now abandoned, which is a continuation-in-part of application No. 08/906,600, filed on Aug. 6, 1997, now abandoned.

(30) Foreign Application Priority Data

| Oct. 9, 1996 | (JP) | ............................................. 8-268863 |
| Aug. 7, 1996 | (JP) | ............................................. 8-208601 |
| Dec. 24, 1997 | (JP) | ............................................. 9-354880 |

(51) Int. Cl.⁷ ............................................. A61K 31/70
(52) U.S. Cl. ........................................... 514/54; 536/53
(58) Field of Search ............................... 536/53; 514/54

(56) References Cited

U.S. PATENT DOCUMENTS

| 4,141,973 A | 2/1979 | Balazs ......................... 424/180 |
| 4,801,619 A | 1/1989 | Linblad ....................... 514/825 |
| 4,920,104 A | 4/1990 | Devore et al. ................ 514/54 |
| 5,140,016 A | 8/1992 | Goldberg ...................... 514/57 |
| 5,190,759 A | 3/1993 | Linblad et al. ............. 424/423 |
| 5,234,914 A | 8/1993 | Gallina ......................... 514/54 |
| 5,409,904 A | 4/1995 | Hecht et al. .................. 514/23 |
| 5,681,825 A | 10/1997 | Lindvquist et al. ........... 514/54 |
| 5,843,025 A | * 12/1998 | Shaari .......................... 602/53 |
| 5,929,050 A | 7/1999 | Petito .......................... 514/54 |
| 6,136,341 A | 10/2000 | Petito ......................... 424/446 |

FOREIGN PATENT DOCUMENTS

| EP | 781547 | 7/1997 |

OTHER PUBLICATIONS

Buckman, R.F., et al., A Physiologic Basis for the Adhesion–free Healing of Deperitonealized Surfaces, *J. Surg. Res.* 21:67–76 (1976).
Raftery, A.J., Effect of Peritoneal Trauma on Peritoneal Fibrinolytic Activity and Intraperitoneal Adhesion Formation, *Eur. Surg. Res.* 13:397–401.
Abe, H., et al., The Effect of Intraperitoneal Administration of Sodium Tolmetin–Hyaluronic Acid on the Postsurgical Cell Infiltration in Vivo, *F. Surg. Res.* 49:322–27 (1990).
Manuskiatti et al., Hyaluronic Acid And Skin:Wound Healing and Aging, *International Jour. of Dermatology* 35(8):539–544 (Aug., 1966).
*Principles of Surgery*, 7th ed. (Schwartz et al., eds.), McGraw–Hill (1999), pp. 270–271.

* cited by examiner

*Primary Examiner*—Kathleen K. Fonda
(74) *Attorney, Agent, or Firm*—Richard C. Litman

(57) ABSTRACT

A method for decreasing or shortening the length of time required to complete a surgical procedure by the application of hyaluronic acid to the surgical site, and for wound management by topical application of hyaluronic acid to a wound by syringe through a thin film dressing. The method of wound management results in accelerated wound healing time. The solution of hyaluronic acid may include an effective amount of a polysulfated glycosaminoglycan for stimulating macrophage activity at the surgical wound site.

28 Claims, No Drawings

METHOD FOR USE OF HYALURONIC ACID IN WOUND MANAGEMENT

CROSS-REFERENCE TO RELATED APPLICATIONS

The present application is a continuation-in-part of my prior application Ser. No. 09/219,456, filed Dec. 23, 1998, now abandoned, which is a continuation-in-part of application Ser. No. 08/906,600, filed Aug. 6, 1997, now abandoned.

BACKGROUND OF THE INVENTION

1. Field of the Invention

The present invention relates to a method of expediting surgical procedures, and more specifically to a method of decreasing or shortening the length of time required to complete a surgical procedure by the application of hyaluronic acid to the surgical site, as well as to a method of wound management (whether a surgical wound or otherwise) by the use of a hyaluronic acid composition for decreased healing time and improved wound healing.

2. Description of Related Art

The expression "time is of the essence" has no more greater meaning or impact than when applied to a surgical procedure. Every second saved in reducing the length of time required to complete a surgical procedure can make the difference between life or death for the patient. Therefore, the length or duration of time required by a surgeon to finish a surgical procedure is a critical factor in determining the successful outcome of a surgical procedure. If a surgeon can shorten the length of time required to complete a surgical procedure, and thereby shorten the length of time a patient must be under anesthesia, in particular general anesthesia, the more likely the surgical procedure will attain the desired successful end result.

Various attempts have been made in the field of surgical medicine to develop ways to decrease or shorten the duration or length of time required to a complete surgical procedure. One such development pertains to the use of laparoscopy, or similar methods, that are less invasive, generally require less time to accomplish the same surgical goals when compared to standard nonlaparoscopy based surgical procedures, and promote a faster rate of recovery for the patient. However, laparoscopy or similar methods generally require equipment that can be very expensive; are not always readily available; often require special training and experience to become proficient in its use; and can not be used or modified in all surgical procedures. Therefore, what is needed is a method that decreases or shortens the duration or length of time required to complete any surgical procedure and that is relatively inexpensive and easy to use; does not require additional training or equipment to use; and is applicable to wide variety of surgical procedures, including laparoscopy or similar such methods.

The present inventor has unexpectedly found a way of accomplishing the above goals by decreasing or shortening the duration or length of time required to complete surgical procedures by the application of hyaluronic acid, or any pharmaceutically acceptable salt thereof such as sodium hyaluronate, into a surgical site in order to coat tissue exposed by the surgical procedure.

Hyaluronic acid (hereinafter referred to as HA) is a naturally occurring high viscosity glycosaminoglycan (GAG) having alternating β1–3 glucouronidic and β1–4 glucosaminidic bonds. HA has a broad ranging molecular weight, which is generally accepted to range between about 50,000 and 8,000,000 (or greater) depending upon its source and method of isolation. HA is found in animal tissue (i.e., umbilical cord, skin, vitreous humor, synovial fluid, and rooster combs) and it also can be obtained through fermentation by hemolytic streptococci groups A and C.

Numerous therapeutic uses for HA have been developed for the treatment of a wide range of problems, none of which pertain to methods of decreasing the duration or length of time required to complete a surgical procedure. U.S. Pat. No. 4,920,104, which issued to Dale P. Devore, David A. Swann and Bernard P. Sullivan on Apr. 24, 1990, teaches the use of a sodium hyaluronate solution as an aid in ophthalmological surgery to minimize the increase in post-operative intra-ocular pressure (P.I.O.), particularly where there is loss of the vitreous during surgery. The solutions used therein preferably have a viscosity between about 45–64,000 centistoke, and the HA has an average molecular weight within the range of 1–2 million Daltons.

European Patent Application No. 781 547 issued to Bunter on Jul. 2, 1997 teaches the use of sodium hyaluronate based ophthalmic formulations for use in eye surgery in order to reduce the toxic effects owing to the operation. The sodium hyaluronate based ophthalmic formulation can also be left "in situ" in the eye, without causing any significant elevation in intra-ocular pressure (P.I.O.).

U.S. Pat. No. 4,801,619, which issued to Gert T. Linblad on Jan. 31, 1989, teaches the use of a HA solution by intra-articular injection for controlling joint inflammation and reducing proteoglycan degradation. The solution used therein contains <2.0% HA, with an average molecular weight between about 3–7 million Daltons.

Macromolecular solutions containing HA, for example, have been popular substances in the effort to prevent tissue adhesion and aid in wound healing. It is well known that undesired tissue damage results from most surgical procedures, where cutting, desiccation, ischemic, and manipulative abrasions occur. Suture lines at closed incisions, as well as areas of abrasive contacts that occur between tissue surfaces and the many devices used in surgery (i.e., clamps, gloves, sponges, etc.) are known to be problematic, and often painful sites, which result from damaged cell membrane surfaces. Raftery, A. J., *Effect of Peritoneal Trauma on Peritoneal Fibrinolytic Activity and Intraperitoneal Adhesion Formation, Eur. Surg. Res.* 13:397–401 (1981); Buckman, R.F., et al., *A Physiologic Basis for the Adhesion-free Healing of Deperitonealized Surfaces, J. Surg. Res.* 21:67–76 (1976).

Furthermore, research has shown that the viscous HA macromolecule mechanically stops the oozing from disrupted microvasculi, and preliminary studies indicate that HA coats the peritoneum to suppress post-surgical bleeding. Abe, H., et al., *The Effect of Intraperitoneal Administration of Sodium Tolmetin-Hyaluronic Acid on the Postsurgical Cell Infiltration in Vivo, F. Surg. Res.* 49:322–27 (1990).

U.S. Pat. No. 4,141,973, which issued to Endre A. Balazs on Feb. 27, 1979, discloses an ultra-pure HA fraction that has, among its many uses, the prevention of scar tissue formation and adhesion following surgery by introducing an HA solution into the surgical site, either during surgery or postoperatively. In addition, Balazs contends that HA solutions serve as a mechanical protector of the tissue during surgical manipulation and postoperatively.

U.S. Pat. No. 5,234,914, which issued to Damian Gallina on Aug. 10, 1993, teaches the use of an HA solution for the treatment of hemorrhoids and anorectal diseases which are accompanied by traumatized tissue. The HA solution may contain between 0.01–25.0% HA, which is applied topically to the effected tissues. By adhering to the anorectal epithelium and rectal mucosa, the HA solution provides a reduction in the pain, burning, inflammation, itching, and swelling associated with the above causes.

U.S. Pat. No. 5,190,759, which issued to Gert Linblad and Peter Buckley on Mar. 2, 1993, teaches the use of an HA solution, alone or in combination with dextran, for preventing adhesions between body tissues following surgical procedures. The HA solutions used therein contained between 0.5–6% HA and have a molecular weight within the range of 500,000 and 6,000,000 Daltons.

U.S. Pat. No. 5,409,904, which issued to Gerald Hecht and Ole J. Lorenzetti on Apr. 25, 1995, teaches the use of an HA solution, either alone or in combination with other viscoelastic substances, for preventing post-operative adhesions between healing tissues by introducing the solution into a surgical site during surgery or postoperatively. No mention is made, however, as to the timing of HA solution introduction during the surgical process.

U.S. Pat. No. 5,681,825, which issued to Lindqvist et al. on Oct. 28, 1997 teaches the use of an HA solution into the site of the surgical operation, for facilitating surgical operations that involve the eye or eye area.

U.S. Pat. No. 5,140,016, issued to Goldberg on Aug. 18, 1992 teaches the use of HA based compositions and improved methods for preventing adhesions during surgery.

While the above discussed references contain numerous examples of various medical and surgical uses for HA, none of the references teach or even suggest actually decreasing the length of time or duration required to complete a surgical procedure by using an HA solution. Thus, there is a need for a way in which the length of time required to complete a surgical procedure can be decreased or reduced by the application of a HA solution to a surgical site.

In another aspect, the present invention relates to a method of using hyaluronic acid in wound management. A solution of hyaluronic acid, either alone or in combination with other glycosaminoglycans, and preferably a polysulfated glycosaminoglycan, may be injected by syringe at specified times through a dressing which is maintained over the wound for a period of time which is longer than conventional methods of wound management, promotes quicker wound closure and healing with fewer adverse side effects. Under conventional methods of wound management, a dressing is applied to the wound, and subsequently the protocol calls for removing the dressing, cleansing the wound, and redressing the wound, a procedure which is normally repeated every 24 hours, By contrast, according to the method of the present invention, the dressing remains in place for periods up to between 72 and 86 hours. Various advantages in treating wounds with hyaluronic preparations, other than preventing the formation of adhesions, have been noted, as exemplified by the following patents and publications, but the method of the present invention has not previously been taught or suggested.

U.S. Pat. No. 5,929,050, issued Jul. 27, 1999 to the present inventor, teaches a composition and method for wound treatment, the method comprising administering an effective amount of an aqueous solution of chondroitin sulfate to an open wound to increase the rate of healing. The composition may also include an effective amount of sodium hyaluronate for aiding anti-inflammatory response. U.S. Pat. No. 6,136,341, issued Oct. 24, 2000 to the present inventor, describes a tissue adhesive compound containing hydrolyzed Type I collagen having a molecular weight between 1,000 and 10,000. It is noted that the tissue adhesive compound may be used in combination with hyaluronic acid and glycosaminoglycans to speed the healing process further. The method of using the compound, however, teaches reapplication of the compound and a nonstick dressing at least once every twenty-four hours.

Manuskiatti et al. describe the relation between hyaluronic acid and wound care in "Hyaluronic Acid and Skin:Wound Healing and Aging", *International Jour. of Dermatology*, 35(8) :539–544 (August, 1996) , wherein it is noted at pp. 540–541 that "The facilitating effect of HA [hyaluronic acid] exogenously applied was a surprising observation in wound healing . . . ", citing studies which showed enhanced epithelial migration and differentiation, accelerated wound healing, reduced tissue fibrosis, reduced wound-induced exravasation, and accelerated wound closure. In *Principles of Surgery*, 7th ed., (Schwartz et al., eds.), McGraw-Hill (1999), pp. 270–271, it is speculatively proposed that the application of hyaluronic acid to adult wounds may transform wound healing "into the regeneration-like response seen in the fetus", and it is noted in Table 8-3 that hyaluronic acid functions to provide a fluid environment for cell movement and differentiation, and binds to cytokines. However, no protocol for the topical administration of hyaluronic acid is disclosed.

None of the above inventions and patents, taken either singly or in combination, is seen to describe the instant invention as claimed.

SUMMARY OF THE INVENTION

In one aspect, the present invention pertains to a method of decreasing or shortening the length of time required to complete a surgical procedure, by introducing an hyaluronic acid (HA) solution in order to coat tissue exposed at a surgical site. The method for decreasing the length for a surgical procedure includes using a HA solution having a HA concentration of at least 0.5% (by weight), and wherein the HA has a relative molecular weight of at least approximately $0.75 \times 10^6$ Daltons.

The rapid coating of tissue exposed at the surgical site expedites the surgical procedure by decreasing the length of time required to complete the surgical procedure, as well as facilitates easier handling of the tissue, and minimizes tissue traumatization and post-operative adhesion. In addition, because the HA solution is clear it does not interfere with the visual appearance of tissues at the surgical site. Furthermore, it is biocompatible so it does not need to be removed before closing of the surgical site.

In another aspect, the present invention relates to a method of wound management, including steps of cleaning a wound (debriding when necessary), applying a dressing, preferably a generic thin film dressing, applying a composition of hyaluronic acid to the wound through the dressing using a syringe, monitoring the wound for the development of wound closure and the development of granulation tissue, reapplying the solution when growth of granulation tissue is too rapid and too extensive; and removing the dressing after wound closure. Preferably the solution of hyaluronic acid consists of an aqueous solution of purified hyaluronic acid having a molecular weight of between $0.1 \times 10^6$ to $4.0 \times 10^6$ and a concentration of 0.01 to 65% by weight of the solution, and sodium chloride at a concentration of between 0.01 to 1.5% by weight. A polysulfonated glycosaminoglycan, preferably chondroitin sulfate, made be added to the solution in an amount effective to enhance the proliferation of macrophages at the site of the wound.

Accordingly, it is a principal object of the invention to provide a method of using an HA solution which shortens the length of time required to complete surgical procedures.

It is another object of the invention to provide a method of using an HA solution for the purpose of minimizing tissue damage that arises from handling tissues during surgical procedures.

Yet another object of the invention is to provide a method of using an HA solution which minimizes desiccation of tissues exposed during surgical procedures.

Still another object of the invention is to provide a method of wound management which includes a method of delivering an HA solution to a wound which accelerates wound healing and wound closure time.

It is another object of the invention to provide a method of wound management which saves time and treatment cost by eliminating the necessity for repeated removal of wound dressings and wound cleansing during healing of the wound.

It is a further object of the invention to provide a method of wound management which accelerates wound healing by delivering a solution of hyaluronic acid in combination with a polysulfated glycosaminoglycan for stimulating an immune system response to aid in controlling bacterial infection and contribute to new tissue growth.

It is also an object of the invention to provide a method which is dependable and fully effective in accomplishing its intended purposes.

These and other objects of the present invention will become readily apparent upon further review of the following specification.

DETAILED DESCRIPTION OF THE PREFERRED EMBODIMENT

The present invention relates to a method for decreasing the length or duration of time required to complete a surgical procedure by using hyaluronic acid (HA) solution at surgical wound sites in mammals. The coating and recoating of tissue exposed at the surgical site with a HA solution before, during and after a surgical procedure, expedites the surgical procedure by decreasing the length of time required to complete a surgical procedure. While the use of HA is known to improve tissue handling, minimize tissue traumatization and post-operative adhesions, and inhibit the occurrence of acute inflammatory response, the underlying reason why the use of HA can shorten the length of time require to complete a surgical procedure is not completely understood.

It is preferable to use an HA solution comprising sterile $H_2O$ and at least 0.5% HA (by weight). It is more preferable to use an HA solution comprising sterile $H_2O$, HA in an amount between 0.5–1.5%, sodium chloride in an amount between about 3.0 mg and 10.0 mg, and phosphate buffer to adjust pH to between about 6.2 and 7.1. It also is preferable to use a high molecular weight HA, and more preferably HA having a molecular weight of at least approximately than $0.75 \times 10^6$ Daltons. Even more preferable is an HA solution containing HA with a molecular weight within the range of about $0.75$–$1.2 \times 10^6$ Daltons. However, where an HA solution containing less than 1.0% HA is used to decrease the length or duration of time required to complete a surgical procedure according to the present invention, it is preferable to utilize HA having a molecular weight greater than about $1.0 \times 10^6$ Daltons. The following composition, however, is most preferred for use with decreasing the length or duration of time required to complete a surgical procedure according to the present invention:

| Component | Amount |
| --- | --- |
| Hyaluronate, sodium salt MW > $0.75 \times 10^6$ Daltons | 1.0% (weight) |
| NaCl | 7.3 mg |
| $PO_4^{2-}$ Buffer | pH to 6.9 |
| Sterile $H_2O$ | QS to vol. 6 ml |

Any pharmaceutically acceptable form of HA may be used with the present invention. Compositions used with the method of the present invention typically will be selected from the group consisting of HA, potassium hyaluronate, or sodium hyaluronate. However, these compositions in no way limit the forms of HA that can be employed with the present invention.

According to the present invention, the method for expediting a surgical procedure by decreasing the length or duration of time required to complete a surgical procedure by using hyaluronic acid (HA) solution at surgical wound sites in mammals involves the following steps, and which are applicable to surgical procedures on all mammals.

As with all conventional surgical procedures, it is necessary to prepare the surgical site by sterilizing the area where an incision is to be made, and administer any local or general anaesthetic to the patient. Following preparation of the surgical site, the surgeon opens the site with one or more incisions and exposes the site to be entered by the surgical team.

The duration or length of time required to complete a surgical procedure can be shortened by initially applying an HA solution immediately following exposure of the tissue at the surgical site, but prior to the time the surgeon actually enters the surgical site. An HA solution of at least 0.5% HA (by weight) and containing HA having a molecular weight of preferably about $1.0 \times 10^6$ Daltons is rapidly applied to the surgical site for quickly and accurately coating tissue exposed during the surgical procedure. In order to rapidly apply the HA solution, it is preferable to utilize a syringe containing approximately 6 milliliters of the HA solution. The syringe is manipulated by the surgeon or another member of the surgical team to cause the solution to be dispersed onto the selected tissue sites, thereby coating the selected tissue appropriately with the HA solution. Other means for delivering the HA solution onto selected tissue at the surgical site can be selected, including, but not limited to, spraying the HA solution from a spray bottle, pouring the HA solution from a container such as a vial, and applying the solution to the surgeon's gloves. Depending upon the size of the surgical site, the tissue involved, and the invasiveness of the procedure, more or less than 6 milliliters of the HA solution may be used to coat the exposed tissue. Thus, in performing this step of a preferred embodiment of the current invention, it may be necessary to introduce varying amounts of the HA solution to ensure adequate and sufficient coverage of tissue exposed at the surgical sites with the HA solution.

While performing the surgical procedure in accordance with conventional medical procedures and techniques, the presence of the HA solution at the surgical site expedites the surgical procedure by decreasing the duration or length of time required to complete the surgical procedure. In addition, because the HA solution is clear it does not interfere with the visual appearance of tissues at the surgical site.

Since each surgical procedure involves a different level of invasiveness and each differs with respect to duration or length of time required to complete the procedure, it is preferable to periodically re-apply the HA solution to exposed tissue at the surgical site by repeating the rapid application of the HA solution used in initially coating tissue exposed at the surgical site. Because the coating of HA on the exposed tissue may be disrupted to some extent by the handling of the tissue during the surgical procedures, it is necessary periodically to reapply a coating of the HA solution in order to maintain coverage of the exposed tissue with the HA solution. Depending upon the length of the surgical procedure and its degree of invasiveness, repeating the application of the HA solution may be necessary up to every 3–12 minutes, and more preferably every 3–8 minutes, and even more preferably every 5–8 minutes. Maintaining a thorough and sufficient HA coating on exposed tissue throughout the surgical procedure enables the surgeon to shorten the length of time required to finish the surgery, while minimizing tissue trauma.

Upon closing the surgical site, it is preferable to leave the HA solution in the surgical site for continued coating of the previously exposed tissues. The HA barrier coating is degradable by the body, and, because it is biocompatible will not result in any adverse reactions. By applying an HA solution to tissue exposed at the surgical site in this manner, the duration or length of time required to complete a surgical procedure can be substantially shortened. The phrase "substantially shortened", as used herein means that the period of time required to complete a particular surgical procedure can be shortened preferably on average by approximately 10 percent or more by applying an HA solution to tissue exposed at the surgical site in manner herein described, when compared to the same surgical procedure performed without the use of the hyaluronic acid solution to coat tissue exposed at the surgical site.

The following examples are included to demonstrate how the duration or length of time required to complete a surgical procedure can be substantially shortened, and to demonstrate techniques discovered by the inventor that function well in the practice of the invention, and therefore, may be considered to constitute a preferred mode for its practice. However, those in the art should appreciate, in light of the present disclosure, that many changes can be made in the specific embodiments which are disclosed and still obtain a like or similar result of decreasing the length of time required to finish the surgical procedure, without departing from the scope of the invention.

EXAMPLES

Example No. 1

An exploratory enterotomy was performed on a two and a half year old female spayed golden retriever. The animal was surgically prepped and anesthetized with a Ketamine and Valium induction, and maintained on Isoflurane and $O_2$. The HA solution had a weight percentage of 1.0% HA with a molecular weight of $1.57 \times 10^6$ Daltons. The HA solution was applied by dropper method immediately following a midline abdominal incision prior to the surgeon entering the surgical site. Repeated application of the HA solution was accomplished by dripping the HA solution onto the affected tissue at 3–4 minute intervals; a total of 18 ml 1.0% HA was used during the surgical procedure. Foreign bodies, including a mop head, a corncob and a baby bottle nipple, were moved into the incision and removed. All edges were trimmed and flushed with saline. Following saline wash, all exposed tissue was coated again with the HA solution to avoid desiccation and to prepare for additional handling. The site was closed as the HA solution was dripped into the closed incision site, covering the exposed tissue fully.

Operating time for this procedure using the HA solution was approximately 145 minutes. It is estimated that the use of the HA solution for this procedure saved approximately 20–35 minutes.

Absent the use of the HA solution in accordance with the method of the present invention, normal operating time for the above procedure is between about 160–180 minutes.

In addition, the tissue condition was vastly improved in that moisture was retained to a very high degree, and the tissue surrounding the trauma site showed minimal trauma. After approximately two weeks, the animal showed excellent healing results with no postoperative pain.

Example No. 2

An exploratory gastronomy was conducted to remove a plastic toy from the stomach of a 2 year old female collie. The animal was surgically prepped and anesthetized with a Ketamine and Valium induction, and maintained on Isoflurane and $O_2$. The HA solution had a weight percentage of 1.0% HA with a molecular weight of $1.25 \times 10^6$ Daltons. A midline abdominal incision was made and the HA solution was immediately dripped via syringe into the surgery field prior to the surgeon entering the surgical site. Repeated application of the HA solution was accomplished by dripping the HA solution onto the affected tissue at 4–5 minute intervals; a total of 18 ml 1.0% HA was used during the surgical procedure. The plastic toy was moved into the incision and removed. Additional HA solution was applied to the area the toy had occupied. The removal of the toy was made easier due to the lubrication and coating action of the HA solution, which render the tissue slippery and highly moisturized. In addition, it was apparent that the tissue damage was minimized due to the ease of the toy removal. The incision site was then coated with additional HA solution and closed.

Operating time for this procedure using the HA solution was approximately 58 minutes. It is estimated that the use of the HA solution for this procedure saved approximately 10–20 minutes. Absent use of the HA solution in accordance with the method of the present invention, normal operating time for the above procedure is between about 67–80 minutes.

In addition, excellent healing response occurred with no postoperative complications of pain, and the overall tissue condition was vastly improved over non-use of the HA solution.

Example No. 3

An intestinal (colon) resection/anastomosis was performed in a three hour old male Old English Sheepdog puppy. The animal was surgically prepped and anesthetized with a Ketamine and Valium induction, and maintained on Isoflurane and $O_2$. The HA solution had a weight percentage of 1.0% HA with a molecular weight of $0.9 \times 10^6$ Daltons. An incision was made rostral and caudal to umbilicus, midline abdominal, with a colon resection. Immediately following incision, the HA solution was dripped into the surgery field. Repeated application of the HA solution was accomplished by dripping the HA solution onto the affected tissue at 5–6 minute intervals; a total of 30 ml 1.0% HA was used during the surgical procedure. The bowel was appropriately resected and following anastomosis the intestine was replaced into the abdomen. Only internal sutures were coated with the HA solution.

Operating time for this procedure using the HA solution was approximately 78 minutes. It is estimated that the use of the HA solution for this procedure saved approximately 10 minutes. Absent the use of the HA solution in accordance with the method of the present invention, normal operating time for the above procedure is between about 85–95 minutes.

In addition, the application of the HA solution to the bowel allowed the bowel to be handled easily and the coating of HA solution aided to prevent tissue desiccation, thereby preserving affected tissues. Healing time was observed to be extremely short, as the puppy was active in two days and eating in 24 hours. Normal postoperative adhesions in this model are very high, occurring in more than 65% of animals. No postoperative adhesions were evident.

Example No. 4

An enterotomy was performed on a ten year old female spayed domestic short hair cat to remove a corn cob fragment that was causing an obstruction of the distal duodenum. The animal was surgically prepped and anesthetized with a Ketamine and Valium induction, and maintained on Isoflurane and $O_2$. The HA solution had a weight percentage of 1.0% HA with a molecular weight greater than $0.75 \times 10^6$ Daltons. A midline abdominal incision was made, with enterotomy and intestinal anastomosis. An obstruction was present for greater than 48 hours, therefore structural tissue damage was evident. To avoid further structural damage to the duodenum, the HA solution was initially applied to the surgeon's latex gloves. Repeated application of the HA solution was accomplished by dripping the HA solution onto the affected tissue at 7–10 minute intervals; a total of 30 ml 1.0% HA was used during the surgical procedure. The corn cob fragment was removed from the duodenum and additional HA solution was applied to the damaged site.

Operating time for this procedure using the HA solution was approximately 75 minutes. It is estimated that the use of the HA solution for this procedure saved approximately 10–20 minutes. Absent the use of the HA solution in accordance with the method of the present invention, normal operating time for the above procedure is between about 85–95 minutes.

In addition, the use of HA to coat the surgeon's gloves resulted in slightly impaired handling of the tissue, but it significantly minimized further damage to the tissue structure. Removal of the foreign object was made less invasive by use of the HA solution, and the entire surgical site (i.e., all exposed tissues) was preserved by the coating action of the HA solution. The cat healed very well with no problems as may have been associated with extensive damage to the tissue structure. Healing time was reduced from a normal 5–7 days to about 3–4 days.

Example No. 5

A colostomy was conducted to remove a hairball obstruction in an eight year old obese, female spayed domestic short-hair cat. The animal was surgically prepped and anesthetized with a Ketamine and Valium induction, and maintained on Isoflurane and $O_2$. The HA solution had a weight percentage of 1.0% HA with a molecular weight of $1.3 \times 10^6$ Daltons. A midline abdominal incision was made at the cecocolic junction, with enterotomy and intestinal anastomosis. Following incision, the HA solution was immediately dripped onto the site and subsequently the colon as it rested outside the abdomen. Repeated application of the HA solution was accomplished by dripping the HA solution onto the affected tissue at 5–7 minute intervals; a total of 30 ml 1.0% HA was used during the surgical procedure. While the colon was removed from the abdomen, it was heavily coated at the same intervals. Following removal of the obstructed portion of the colon, the colon was reattached to close the colostomy site and HA solution was applied to the internal sutures.

Operating time for this procedure using the HA solution was approximately 70 minutes. It is estimated that the use of the HA solution saved approximately 20 minutes in the performance of this procedure. Absent the use of the HA solution in accordance with the method of the present invention, normal operating time for the above procedure is between about 90–120 minutes.

In addition, the application of the HA solution acted as a protective tissue coating, protecting the tissue from drying out and from tissue trauma that occurs when handling the organ. The procedure was speeded by the application of the HA solution, allowing more rapid movement with minimal tissue damage.

Example No. 6

An ileo resection of the ileocecocolic junction was performed on a twelve year old male neutered Siamese cat. The animal was surgically prepped and anesthetized with a Ketamine and Valium induction, and maintained on Isoflurane and $O_2$. The HA solution had a weight percentage of 1.0% HA with a molecular weight of $1.5 \times 10^6$ Daltons. A midline abdominal incision was made, with anastomosis from jejunum to colon, and the HA solution was immediately dripped onto the site. Repeated application of the HA solution was accomplished by dripping the HA solution onto the affected tissue at 5–6 minute intervals; a total of 18 ml 1.0% HA was used during the surgical procedure. As the bowel rested outside the abdomen, the HA solution was applied at the same intervals. The bowel was appropriately resected and the intestine was placed back into the abdomen. The HA solution was applied to the internal sutures.

Operating time for this procedure using the HA solution was approximately 70 minutes. It is estimated that the use of the HA solution saved approximately 10 minutes in the performance of this procedure. Absent the use of the HA solution in accordance with the method of the present invention, normal operating time for the above procedure is about 80 minutes.

In addition, the application of the HA solution to the bowel allowed the bowel to be handled easily and the coating of HA solution aided to prevent tissue desiccation, thereby preserving affected tissues. The healing time, given the age of the animal, was notable as no postoperative problems occurred.

Not only may a solution of hyaluronic acid be used to decrease surgical time, but according to another aspect of the present invention, a solution of hyaluronic acid may be used to decrease wound healing time, whether the wound is a surgical wound or otherwise. Traditionally a wound is cleansed, debrided if necessary, look and an appropriate dressing is applied. Usually the dressing is removed and the wound is checked for infection, cleansed, and a new dressing is applied, frequently every twenty-four hours.

However, according to the present invention, the time required for wound healing may be accelerated by the topical application of a composition containing hyaluronic acid to the wound. Preferably the composition is an aqueous solution containing hyaluronic acid having a molecular weight between $0.1 \times 10^6$ to $4.0 \times 10^6$ at a concentration of between 0.01 to 65% by weight and a pH of between 5.0 to 8.0, although a composition having hyaluronic acid with a molecular weight between $0.01\times10^6$ and $12\times10^6$ and having a concentration of HA up to 100% is within the scope of the present invention. The solution also preferably contains between 0.01 to 1.5% sodium chloride by weight. The solution is used promptly after surgically or chemically debriding a wound site, either acute or chronic, for a period of four to six days, or on a clean wound site. Use of the solution is stopped when granulation tissue is seen for two to three days, or when the growth of granulation tissue is too rapid or in too great a quantity.

The wound is best managed by covering the wound with a generic thin film wound dressing (cast polyurethane). The thin film dressing is preferably transparent. The solution of hyaluronic acid is dispensed by syringe through the wound dressing for topical application. In this manner, the development of wound healing may be monitored without removal of the dressing. In controlled mice studies conducted at DeSales University, the wound dressing was kept in place for periods up to seventy-two to eighty-six hours. Leaving the dressing in place helped to control bacterial invasion, left the wound bed undisturbed, negated environmental factors, stabilized wound temperature, and improved cell function. Eliminating the necessity for frequent changes in the wound dressing resulted in economic savings, and healing time was reduced over traditional methods.

While injection of HA in aqueous solution by syringe is the preferred method of delivering HA to the wound site, it will be understood that HA may be delivered in a composition formulated as a powder, a gel, or a cream which can be injected or infused through the wound dressing. For example, it is possible to deliver HA to the wound site through a membrane, or a fleece or patch dressing, the HA being cross-linked with a copolymer to provide a reservoir which may be time released to the wound site according to a predictable schedule.

When the hyaluronic acid solution is used topically during the last two to three days of wound closure, removal of the wound dressing is eased. The viscosity and lubricating properties of high molecular weight HA allow the dressing to be removed without fear of re-opening any acute (surgical) or chronic wound site.

It has also been found that HA, when combined with other polysulfonated glycosaminoglycans, e.g., chondroitin sulfate, promotes the proliferation of macrophages at the wound site, thereby resulting in enhanced control of bacterial infection and accelerating wound healing. Further, the beneficial effects of the composition may be increased by adding collagen, either natural or enhanced, to the composition.

It is postulated that application of the HA composition according to the method of the present invention results in greater tissue strength as compared to conventional wound treatment methods. The composition provides HA, which is essential for cell proliferation and migration. The water binding properties of HA may serve as a means for water hemostasis in the skin. The methodology and use of HA provides the ability to modulate the repair of tissue, thereby decreasing wound healing time and accelerating the growth of healthy tissue for improved wound healing. The HA composition serves as a cell protectant or tissue protectant, cushioning the wound from mechanical injury during the healing process.

Accordingly, a method of wound management may be stated to include the steps of cleaning a wound (debriding when necessary), applying a dressing, preferably a generic thin film dressing, applying a solution of hyaluronic acid to the wound through the dressing using a syringe, monitoring the wound for the development of wound closure and the development of granulation tissue, reapplying the solution when growth of granulation tissue is too rapid and too extensive; and removing the dressing after wound closure. Preferably the solution of hyaluronic acid consists of an aqueous solution of purified hyaluronic acid having a molecular weight of between $0.1\times10^6$ to $4.0\times10^6$ and a concentration of 0.01 to 65% by weight of the solution, and sodium chloride at a concentration of between 0.01 to 1.5% by weight. A polysulfonated glycosaminoglycan, preferably chondroitin sulfate, made be added to the solution in an amount effective to enhance the proliferation of macrophages at the site of the wound.

It is to be understood that the present invention is not limited to the sole embodiment described above, but encompasses any and all embodiments within the scope of the following claims.

I claim:

1. A method for wound management of an open wound, comprising the steps of:
    (a) cleaning a wound;
    (b) applying a dressing to the wound;
    (c) applying a solution of hyaluronic acid to the wound through the dressing using a syringe;
    (d) monitoring the wound for the development of wound closure and the development of granulation tissue; and
    (e) removing the dressing after wound closure.

2. The method for wound management according to claim 1, further comprising the step of debriding the wound before the step of applying the dressing to the wound.

3. The method for wound management according to claim 1, wherein said dressing is a thin film dressing.

4. The method for wound management according to claim 1, wherein said dressing is a thin film dressing made from cast.

5. The method for wound management according to claim 1, wherein said dressing is transparent.

6. The method for wound management according to claim 1, wherein said solution of hyaluronic acid comprises an aqueous solution of purified hyaluronic acid having a molecular weight of between $0.1\times10^6$ to $4.0\times10^6$ and a concentration of 0.01 to 65% by weight of the solution.

7. The method for wound management according to claim 6, wherein said solution has a pH between about 5.0 and 8.0.

8. The method for wound management according to claim 6, wherein said solution further comprises sodium chloride having a concentration of between 0.01 to 1.5% by weight.

9. The method for wound management according to claim 6, wherein said solution further comprises an effective amount of a polysulfonated glycosaminoglycan for enhancing macrophage activity.

10. The method for wound management according to claim 6, wherein said solution further comprises an effective amount of chondroitin sulfate for enhancing macrophage activity.

11. The method for wound management according to claim 1, wherein said solution of hyaluronic acid consists essentially of an aqueous solution containing:
    purified hyaluronic acid having a molecular weight of between $0.1\times10^6$ to $4.0\times10^6$ and a concentration of 0.01 to 65% by weight of the solution; and
    sodium chloride having a concentration of between 0.01 to 1.5% by weight;
    wherein the solution has a pH of between 5.0 and 8.0.

12. The method for wound management according to claim 1, wherein said solution of hyaluronic acid consists essentially of an aqueous solution containing:

purified hyaluronic acid having a molecular weight of between $0.1 \times 10^6$ to $4.0 \times 10^6$ and a concentration of 0.01 to 65% by weight of the solution;

sodium chloride having a concentration of between 0.01 to 1.5% by weight; and an effective amount of a polysulfonated glycosaminoglycan for enhancing macrophage activity wherein the solution has a pH of between 5.0 and 8.0.

13. The method for wound management according to claim 1, wherein said solution of hyaluronic acid consists essentially of an aqueous solution containing purified hyaluronic acid having a molecular weight of between $0.1 \times 10^6$ to $4.0 \times 10^6$ and a concentration of 0.01 to 65% by weight of the solution;

sodium chloride having a concentration of between 0.01 to 1.5% by weight; and an effective amount of chondroitin sulfate for enhancing macrophage activity wherein the solution has a pH of between 5.0 and 8.0.

14. The method for wound management according to claim 1, further comprising the step of reapplying the solution of hyaluronic acid when growth of granulation tissue is too rapid.

15. The method for wound management according to claim 1, further comprising the step of reapplying the solution of hyaluronic acid when growth of granulation tissue is too extensive.

16. A method for shortening the duration of time required to complete a surgical procedure and for post-surgical wound management, comprising the steps of:

providing a hyaluronic acid solution having a hyaluronic acid concentration of at least 0.5%, and a molecular weight of at least approximately $0.75 \times 10^6$ Daltons;

applying the hyaluronic acid solution to coat tissue exposed at the surgical site following an incision and prior to a surgeon entering the surgical site; and applying the hyaluronic acid solution periodically to maintain a coat of the hyaluronic acid solution on tissue exposed at the surgical site throughout the course of the surgical procedure;

applying a thin film dressing to the post-surgical wound;

applying the hyaluronic acid solution to the wound through the dressing using a syringe;

monitoring the wound for the development of wound closure and the development of granulation tissue; and removing the dressing after wound closure.

17. The method for shortening the duration of time required to complete a surgical procedure and for post-surgical wound management according to claim 16, wherein the hyaluronic acid solution comprises:

sterile $H_2O$;

hyaluronic acid in an amount of between 0.5% and 65% by weight, and wherein the molecular weight of the hyaluronic acid is between $0.75 \times 10^6$ and $4.0 \times 10^6$;

sodium chloride in an amount between 0.01 to 1.5% by weight; and phosphate buffer to adjust pH to between 6.2 and 7.1.

18. The method for shortening the duration of time required to complete a surgical procedure and for post-surgical wound management according to claim 16, wherein the hyaluronic acid solution further comprises an effective amount of a polysulfonated glycosaminoglycan for enhancing macrophage activity.

19. A method for wound management of an open wound, comprising the steps of:

(a) cleaning a wound;

(b) applying a dressing to the wound;

(c) applying a composition of hyaluronic acid to the wound through the dressing;

(d) monitoring the wound for the development of wound closure and the development of granulation tissue; and (e) removing the dressing after wound closure.

20. The method for wound management according to claim 19, wherein said dressing is a thin film dressing, step (c) further comprising applying the composition of hyaluronic acid by injecting the composition through the dressing using a syringe.

21. The method for wound management according to claim 19, wherein said composition of hyaluronic acid comprises purified hyaluronic acid having a molecular weight of between $0.01 \times 10^6$ to $12 \times 10^6$.

22. The method for wound management according to claim 6, wherein said composition has a concentration of up to 100% by weight.

23. The method for wound management according to claim 19, wherein said solution of hyaluronic acid comprises an aqueous solution of purified hyaluronic acid having a molecular weight of between $0.1 \times 10^6$ to $4.0 \times 10^6$ and a concentration of 0.01 to 65% by weight of the solution.

24. The method for wound management according to claim 23, wherein said solution further comprises sodium chloride having a concentration of between 0.01 to 1.5% by weight.

25. The method for wound management according to claim 19, wherein said composition further comprises an effective amount of a polysulfonated glycosaminoglycan for enhancing macrophage activity.

26. The method for wound management according to claim 19, wherein said composition further comprises an effective amount of collagen for improved tissue strength.

27. The method for wound management according to claim 19, wherein said dressing comprises a patch, and wherein said composition comprises hyaluronic acid cross-linked with an effective amount of a copolymer for providing the hyaluronic acid to a wound site on a time release basis.

28. The method for wound management according to claim 19, wherein said composition of hyaluronic acid is contained in a formulation selected from the group consisting of an aqueous solution, a powder, a gel, and a cream.

* * * * *